(12) United States Patent
Yamashita et al.

(10) Patent No.: US 7,838,631 B2
(45) Date of Patent: Nov. 23, 2010

(54) APPARATUS FOR MEASURING HIGH DENSITY LIPOPROTEINS AND METHOD OF SEPARATING HIGH DENSITY LIPOPROTEINS

(75) Inventors: Kotaro Yamashita, Mito (JP); Masafumi Miyake, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 52 days.

(21) Appl. No.: 12/131,438

(22) Filed: Jun. 2, 2008

(65) Prior Publication Data
US 2008/0312414 A1    Dec. 18, 2008

(30) Foreign Application Priority Data
Jun. 4, 2007    (JP) .............................. 2007-148116

(51) Int. Cl.
*C07K 14/775*    (2006.01)
*C07K 1/30*    (2006.01)
(52) U.S. Cl. ........................ 530/359; 530/412; 530/419; 422/82.01
(58) Field of Classification Search ................ 530/359, 530/412, 419; 422/82.01
See application file for complete search history.

(56) References Cited

U.S. PATENT DOCUMENTS 5,426,030 A    6/1995    Rittersdorf

2003/0175153 A1    9/2003    Anaokar
2003/0224471 A1    12/2003    Jones et al.

FOREIGN PATENT DOCUMENTS

| EP | 319 250 | 6/1989 |
| JP | 2-210265 | 8/1990 |
| JP | 3-099268 | 4/1991 |
| WO | WO 88/05912 | 8/1988 |
| WO | 2006067424 A1 | 6/2006 |

OTHER PUBLICATIONS

European Patent Office, "European Search Report" for European Application No. 08 01 0052, Mar. 10, 2009, 9 pages.

*Primary Examiner*—Chih-Min Kam
(74) *Attorney, Agent, or Firm*—Mattingly & Malur, P.C.

(57) ABSTRACT

The present invention provides a method of separating lipoproteins other than high density lipoproteins from a biological fluid. The method can quickly measure HDL cholesterol with a simple configuration and without the need of providing additional complicated devices. In this method, high density lipoproteins not generating any precipitate are fractionated from low density lipoproteins, very-low density lipoproteins, and chylomicrons generating precipitates. Then the precipitates are removed not by centrifugal separation based on the conventional technology, but by filtration using a filter to separate high density lipoproteins in blood serum. A hydrophilic cellulose-mixed ester is preferable as a material for the filter, and the pore diameter is 0.8 μm or below. When the filtering method is employed, it is possible to eliminate the complicated operations required in the conventional centrifugal separation, and to shorten the time it takes for separation of the high density lipoproteins.

2 Claims, 5 Drawing Sheets

APPARATUS FOR MEASURING HIGH DENSITY LIPOPROTEINS AND METHOD OF SEPARATING HIGH DENSITY LIPOPROTEINS

BACKGROUND OF THE INVENTION

1. Field of the Invention

The present invention relates to a separation unit, and particularly to an apparatus for separating a specific component in a fluid. More particularly, the invention relates to an apparatus for separating a specific component, more specifically a lipid component contained in a high density lipoprotein (abbreviated as HDL hereinafter) fraction in a biological fluid such as blood. Furthermore, the present invention relates to a method and an apparatus for separating and measuring high density lipoproteins, which is used for measurement of such a component.

2. Background of the Invention

A method of separating a high density lipoprotein is disclosed in, for instance, JP-A-3-99268.

Because the HDL cholesterol in blood is a factor for coronary atherosclerosis prevention, measurement of the HDL cholesterol is performed as part of medical check for lifestyle-related diseases prevention in many facilities.

A total cholesterol in blood, plasma, and serum is one of well-known parameters used to estimate the risk relating to a degree of coronary artery diseases.

However, the concentration of the total cholesterols is the only defined value to estimate the risk of individual developing diseases.

It is more significant to measure both an amount of low density lipoproteins and an amount of high density proteins.

In the epidemiological and clinical studies, it has been clarified that there is a positive relationship between the LDL cholesterol and the coronary artery diseases, and also that there is a negative relationship between the HDL cholesterol and the coronary artery disease.

Because the relationship between the total cholesterol and the coronary artery disease is analogous to that between the HDL and the coronary artery disease, measurement of the HDL and total cholesterol is required for estimation of the risk of coronary artery diseases.

Such measurement as described above is advantageously employed in a wide range for diagnosis of coronary artery diseases.

HDL cholesterol is currently checked by fractionating HDL from other lipoproteins and measuring an amount of HDL cholesterol in the supernatant liquid by the enzyme method or the like.

To measure HDL cholesterol independently, it is necessary to separate other lipoproteins (LDL, VLDL (very low density lipoprotein), chylomicron) present in a biological sample. Embodiments of separation of lipoproteins other than HDL include a method making use of different surface charges (electrophoresis by using paper or agarose as a carrier) or a method making use of differences in apoliproteins (epidemiological method of using a specific antibody).

Furthermore, there are a method making use of a ultracentrifugal force, and a method of precipitating and removing lipoproteins other than HDL by using bivalent metal ions and polyanion.

Because it is necessary to use an ultracentrifugal separator in the ultracentrifugal force method, operation on the ultracentrifugal separator is complicated and it takes a long period of time. Therefore, a method of fractionating HDL used for measurement is mainly a precipitation method.

As a polyanion precipitant based on a combination of a bivalent metal ion and a polyanion, such combinations as heparin-$Ca^{2+}$, heparin-$Mn^{2+}$, phosphotungustic acid-$Mg^{2+}$, and dextran sulfate-$Mg^{2+}$ are used.

The methods making use of the polyanion precipitant have the following common feature.

Specifically, any of the precipitants described is added to serum and is left for 5 to 20 minutes (the time varies according to a precipitant used) so that a sufficient amount of precipitate is generated, and then centrifugal separation is performed for 10 to 15 minutes at a rotational speed of 3000 rpm. After the centrifugal separation, the supernatant liquid (HDL fraction) is extracted, and quantification is carried out at 37° C. by cholesterol chromogenic reaction or the enzyme electrode method.

SUMMARY OF THE INVENTION

As described above, however, the method of measuring HDL cholesterol by making use of a precipitant has the problem that operations for centrifugal separation are required in addition to generation of precipitate, and so the operations are complicated and it takes much time disadvantageously although they are not the same as those required in the ultracentrifugal separation method.

Specifically, even if a net time it takes for centrifugal separation is only 10 minutes, it takes at least 20 minutes because it takes time for removing a sample, preparing a separation tube, balancing for centrifugal separation, and acceleration or deceleration of the rotational speed. Also mix-up of samples might occur.

One of the methods already put into practical use is electrophoresis, although the operational principle is completely different from that of the precipitation method. In this method, lipoproteins are fractionated to HDL, LDL, and VLDL by electrophoresis respectively, and cholesterol in the HDL fraction is stained and quantified by the densitometory. However, it takes a long time for electrophoresis and staining, and even if the operating speed is high, the time it takes for measurement is not substantially different from that in the precipitation method.

The present invention has been made to solve the problems as described above, and it is an object of the present invention to provide a method of quickly separating lipoproteins other than HDL from a biological fluid with a simple configuration and without the need of providing additional complicated devices.

The present invention provides a method of separating lipoproteins other than HDL (High Density Lipoprotein) from a biological fluid, comprising the step of: circulating the biological fluid through a carrier used for separating the lipoproteins other than HDL.

The present invention provides a method of quickly separating lipoproteins other than HDL from a biological fluid with a simple configuration.

DETAILED DESCRIPTION OF THE PREFERRED EMBODIMENTS

Figure 1:
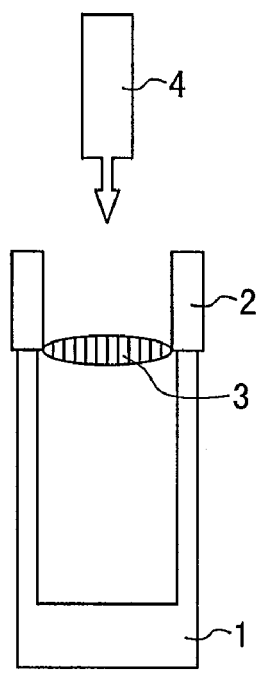
FIG. 1 is a view illustrating a device including a sample vessel and a separation unit such as a filter in Embodiment 3 of the present invention.

Outline of embodiments in the present invention are described below.

The present invention provides a method of separating high density lipoproteins wherein precipitates of low density lipoproteins, very low density lipoproteins and chylomicrons are generated by adding a reagent for precipitation of polyanion to serum, and then the precipitates generated in the above step are removed by filtering.

In a method of quantifying high density lipoprotein cholesterol by using the separation method, high density lipoproteins separated by the separation method are quantified by a calorimetric method or an enzymatic electrode method.

In the present invention, after high density lipoproteins not precipitating is fractionated from low density lipoproteins, very low density lipoproteins and chylomicrons each precipitating by use of a precipitant, precipitates produced with filtrating instead of the conventional centrifugal separation method are removed so that high density proteins are separated from serum.

A filter is preferably made from a hydrophilic cellulose-mixed ester and has a pore diameter of 0.8 μm or below. Adopting a filtering method enables to simplify complicated operations and reduce the time it takes as compared with that in the conventional centrifugal separation method.

In the method of measuring HDL cholesterol according to the present invention, a reagent for precipitation of polyanion is used for fractionating high density lipoproteins from low density lipoproteins, very low density lipoproteins and chylomicrons in the serum, and then the generated precipitates are filtered using hydrophilic filters having a pore diameter of 0.8 μm or below, and then the generated HDL protein fractions are quantified by the calorimetric method or the enzymatic electrode method.

The four precipitants such as heparin-Ca precipitant, phosphotungustic acid-Mg precipitant, dextran sulfate Mg-phosphotungustic acid-Mg precipitant, and isoelectric point fraction-phosphotungustic acid precipitant are widely used as precipitants for polyanions because the materials are excellent in both precision and accuracy in measurement of HDL cholesterols. Any one of these four precipitants can be used in the present invention.

The precipitant can be used in the form of any of a solution, an emulsion, or a suspension. The precipitant are soaked in the filter and then dried. An additive such as a pH buffer material and a surfactant can be used in this method.

Commercially available filter products can be used in this method. Materials used for the filters are cellulose, nylon, polysulfone, and the like. However, a preferable material for the filter is cellulose, more preferably mixed ester of cellulose acetate and nitro cellulose.

Preferably, the filter has a pore diameter of 0.8 μm or below, a film thickness of 50-400 μm, a film weight of 3-10 mg/cm$^2$, and a flow rate (differential pressure 0.07 Mpa) of 90-150 ml/minute/cm$^2$ in the case of water.

Additives such as a surfactant and pH buffer material can be added to the filter in addition to fractionating reagents, if required. In a layer where fractionation filtering is carried out, lipoprotein elements, which are not qualified with fractionating agents, generate precipitates when a reagent solution is dripped, and captured in the constitutional layer. High density lipoprotein components for qualification do not precipitate and penetrate a lower layer.

Especially, a surfactant can effectively be used for adjusting the infiltration speed for instance when a liquid sample is applied to a device according to the present invention.

Either ionic (anionic or cationic) agents or nonionic agents may be used as a surfactant in the present invention, but nonionic ones are more effective.

Embodiments of the nonionic surfactant include ester type of glycerol fatty acid ester, sorbitan fatty acid ester, ether type of polyoxyethylene alkylphenyl ether, polyoxyethylene alkyl ether, and ester ether type of polyethylene glycol fatty acid ester.

Any of the surfactants listed above can be used for adjusting the infiltration rate into a receptive layer of a liquid sample. The surfactant can be used in a wide range, but preferably a weight of the surfactant is about 10% to a weight of the coating liquid.

A sample is brought into contact with a carrier containing a precipitant so that lipoproteins other than HDL are precipitated. Precipitation is completed within 1 minute, and more preferably within about 10 seconds, and the liquid can be taken out from the carrier substance. This operation can be performed continuously or intermittently by using gravity.

Biological fluids from which lipoproteins other than HDL can be separated with the present invention are especially whole blood, serum, and plasma.

The method according to the present invention is more excellent as compared with any other known method also in other points. In the method according to the present invention, it is possible to treat a liquid sample with an extremely small amount. In addition, the apparatus according to the present invention provides quite easy handling.

When a separation pad for blood cells is used at first, it is possible to easily use all types of blood cells and even whole blood. Separation of lipoproteins other than HDL can be performed within 60 seconds.

The method of separating lipoproteins other than HDL according to the present invention is especially suitable for use in quantifying HDL cholesterol on a tested piece.

To achieve the objective, a liquid from which lipoproteins other than HDL have been separated by the method described above is brought into contacted with reagents required or/and useful in a reaction for testing cholesterol for instance.

The reagents may be present on a porous film as a film or in the coated state. Embodiments of such a reagent are known to those skilled in the art.

The present invention is described in detail below with reference to embodiments thereof, but it is to be noted that the present invention is not limited to the embodiments.

Embodiment 1

A membrane disk filter having a diameter of 5 mm and made of hydrophilic cellulose mixture ester was fixed as a filter on a supporting body. A sample vessel is fixed on the state in which the vessel directly contacts the filter. When a sample is added on the filter, a liquid for measurement oozes through the filter and is accumulated on the sample vessel.

In this embodiment, high density lipoproteins were quantified with SP-4430 produced by Arkray SPOTCHEM as a measuring device and also by using SPOTCHEM HDL Cholesterol Kit as a reagent (based on the dextran sulfate magnesium precipitation method).

The HDL cholesterol kit used in measurement is based on the dextran sulfate magnesium precipitation method as a method of fractionating high density lipoproteins, and the high density lipoproteins are fractionated by mixing the sample with a reagent for precipitation and subjecting the mixture to centrifugal separation.

In the embodiment using a filter, the step of centrifugal separation described above was eliminated, and a fractionated liquid of high density lipoproteins was used as a sample as it was so as to quantity the high density lipoproteins.

50 μL of a reagent for fractionating high density lipoproteins (produced by Arkray) was added to a 50 μL Cholestest N calibrator (produced by Daiichi Chemical Co., Ltd.) to precipitate lipoproteins other than HDL. A precipitation liquid was added to a filter and the oozed liquid was processed with the Arkray SPOTCHEM HDL Cholesterol Kit, followed by quantification of the high density lipoproteins.

In a comparative embodiment, a liquid obtained by subjected a precipitation liquid to centrifugal separation (for 10 minutes at the rotational speed of 3000 rpm) was used as a sample, followed by quantification of the high density lipoproteins.

A liquid containing lipoproteins other than HDL was processed with a sheet of filter, which may be made from various materials, and high density lipoprotein was quantified with a combination of the Arkray SPOTCHEM SP-4430 and SPOTCHEM HDL Cholesterol Kit (based on the dextran magnesium sulfate precipitation method). The result is shown in Table 1.

As shown in Table 1, when GN-4, which is a filter made of hydrophilic cellulose mixture ester (nitrocellulose and cellulose acetate), is used, the deviation from a result obtained by the precipitation method is small, and it was confirmed that the GN-4 exhibits excellent effect in fractionation of lipoproteins other than HDL.

TABLE 1

| Product name | Manufacturer | Material | Pore diameter(μ) | Measured value(mg/dl) | Deviation (%) |
|---|---|---|---|---|---|
| Versapor 1200 | Pall Corporation | Hydrophilic acryl polymer with unwoven support | 1.2 | 120 | 266.7 |
| Versapor 800 | | Hydrophilic acryl polymer with unwoven support | 0.8 | 114 | 253.3 |
| GN-4 | | Hydrophilic cellulose mixture ester | 0.8 | 47 | 103.7 |
| Supor | | Hydrophilic polyether sulfone | 0.8 | 100 | 222.2 |
| Nylasorb | | Hydrophilic nylon | 1 | 108 | 240 |
| SP300 | | Hydrophilic polyether sulfone | 2.2 | 122 | 271.1 |
| 450WE4 | | Hydrophilic polyether sulfone | 0.45 | 83 | 184.4 |
| Biodyne A | | Bipolar nylon 6.6 | 0.45 | 87 | 193.3 |
| Biodyne B | | Positively charged nylon 6.6 | 0.45 | 109 | 242.2 |
| MMM2 | | Hydrophilic polyether sulfone | 2.6 | 119 | 264.4 |
| GN-6 | | Hydrophilic cellulose mixture ester | 0.45 | 64 | 142.2 |
| Millipore HV | Millipore | Hydrophilic cellulose | 0.45 | 78 | 173.3 |
| Millipore GV | | Hydrophilic cellulose | 0.22 | 57 | 126.7 |
| Precipitation method | | | | 45 | 100 |

Embodiment 2

Testing was performed under the same conditions as those in Embodiment 1 except that an HDL calibrator (Wako Pure Chemical Corp.) was used. A result is shown in Table 2. Like in Embodiment 1, when GN-4 is used as a filter, the deviation from a result obtained by the precipitation method is small, and it was confirmed that the GN-4 exhibits excellent effect in fractionation of lipoproteins other than HDL.

TABLE 2

| Product name | Manufacturer | Material | Pore diameter(μ) | Measured value(mg/dl) | Deviation (%) |
|---|---|---|---|---|---|
| Versapor 1200 | Pall Corporation | Hydrophilic acryl polymer with unwoven support | 1.2 | 120 | 219 |

TABLE 2-continued

| Product name | Manufacturer | Material | Pore diameter(μ) | Measured value(mg/dl) | Deviation (%) |
|---|---|---|---|---|---|
| Versapor 800 | | Hydrophilic acryl polymer with unwoven support | 0.8 | 126 | 229 |
| GN-4 | | Hydrophilic cellulose mixture ester | 0.8 | 58 | 105 |
| Supor | | Hydrophilic polyether sulfone | 0.8 | 120 | 218 |
| Nylasorb | | Hydrophilic nylon | 1 | 112 | 203 |
| SP300 | | Hydrophilic polyether sulfone | 2.2 | 128 | 232 |
| 450WE4 | | Hydrophilic polyether sulfone | 0.45 | 92 | 167 |
| Biodyne A | | Bipolar nylon 6.6 | 0.45 | 75 | 136 |
| Biodyne B | | Positively charged nylon 6.6 | 0.45 | 122 | 221 |
| MMM2 | | Hydrophilic polyether sulfone | 2.6 | 136 | 247 |
| GN-6 | | Hydrophilic cellulose mixture ester | 0.45 | 61 | 111 |
| Millipore HV | Millipore | Hydrophilic cellulose | 0.45 | 71 | 129 |
| Millipore GV | | Hydrophilic cellulose | 0.22 | 66 | 120 |
| Precipitation method | | | | 55 | 100 |

Embodiment 3

Embodiments of the high density lipoprotein measuring apparatus according to the present invention are described below with reference to FIG. 1 to FIG. 8.

A supporting body 2 is detachably placed on a cylindrical sample vessel 1 having a bottom shown in FIG. 1. The supporting body 2 has a cylindrical form, and has a filter 3 for fractionation provided inside and at a lower portion thereof.

The filter 3 for fractionation is mainly made of a mixture of nitrocellulose and cellulose acetate, and the materials used have fine pores each having a diameter of 0.8 μm or below.

A precipitant for lipoproteins other than HDL is infiltrated in this filter 3 for fractionation to form a carrier. The filter 3 for fractionation is used as a base material for a carrier. The carrier serves as a separation unit.

A sample injection vessel 4 accommodates therein a sample for measurement. The sample is dripped from the sample injection vessel 4 to the filter 3 as a carrier. The sample, which is a biological fluid, circulates through the filter 3 for fractionation with lipoproteins other than HDL separated, and high density lipoproteins flows through the filter 3 for fractionation into the sample vessel 1.

When a carrier thus-prepared by infiltrating the filter 3 for fractionation with a precipitant for lipoproteins is used, lipoproteins other than HDL can quickly be separated from a biological fluid.

Furthermore, because the separation unit is formed of a carrier for the filter 3 for fractionation, any complicated additional device is not required, and the configuration is quite simple. Because of the features, it can easily be handled in actual use.

Figure 2:
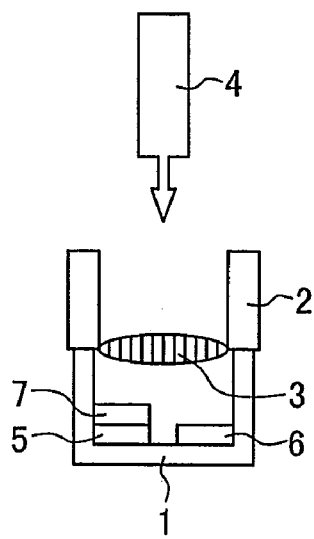
FIG. 2 is a view illustrating a sample vessel having a working electrode and a reference electrode in Embodiment 3 of the present invention.
Figure 3:
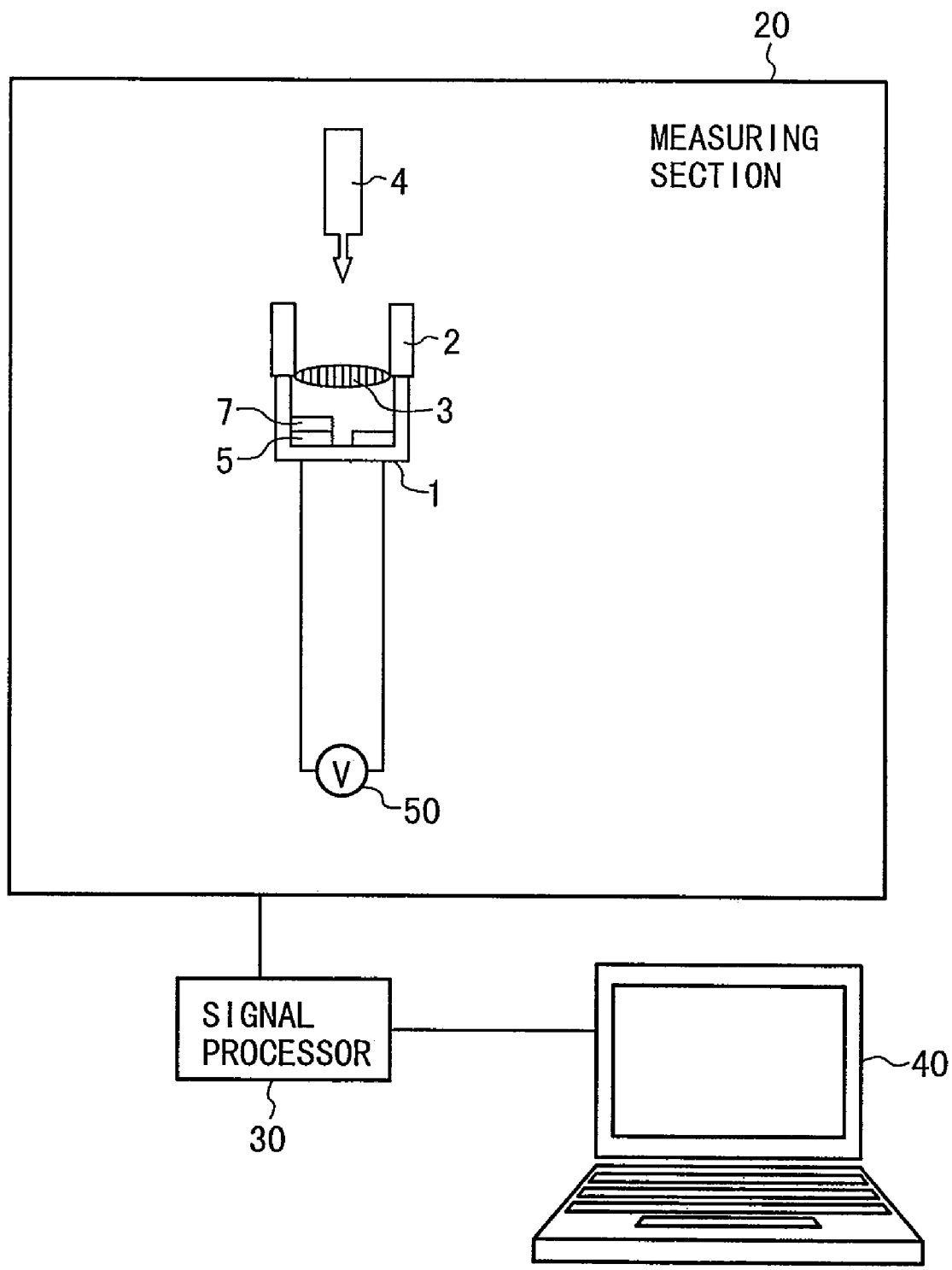
FIG. 3 is an apparatus for measuring high density lipoproteins in Embodiment 3 of the present invention.

FIG. 2 and FIG. 3 are views each illustrating an apparatus for measuring high density lipoproteins.

The apparatus for measuring high density lipoproteins has a measuring section 20, a signal processor 30, and a data processor 40.

The measuring section 20 has a sample vessel 1 and a potentiometer 50.

Provided on a bottom surface of the sample vessel 1 are a working electrode 5 contacting a sample for measurement and a reference electrode 6. A reagent layer 7 is provided on the working electrode 5. The reagent layer 7 reacts with the sample for measurement and contributes to the measurement.

In operation, a sample, which is a biological fluid, is injected into a measurement cell by use of the sample injection vessel 4. The material as an object for measurement precipitated and separated in the sample fluid reacts with a reagent for reaction with the materials to be measured, with the result that an electric charge is generated on a surface of the working electrode 5.

As a result, an interface potential on the working electrode 5 changes. A result of measurement for potential with the potentiometer 50 in the measuring section 20 is monitored in real time by checking changes of the interface potential before and after injection of the sample from the sample injection vessel 4. The result obtained is processed and recorded in the signal processor 30 and in the data processor 40.

Changes on an interface potential on the working electrode 5 depend on a concentration of a material to be measured. Therefore, a concentration of an unknown sample can be obtained from measured values representing changes in potential based on an analytical curve previously prepared by measuring a standard sample which is a standard liquid.

A pressurized liquid feeder can be used as the sample injection vessel 4. In addition, to reduce influence caused by adsorption of foreign materials onto a surface of an electrode when components of a biological sample are measured, a linear polymer may physically be adsorbed in the electrode to form a protective film thereon.

Any of methyl cellulose, acrylamide, dextran, polyethylene glycol, or the like may be used as the linear high polymer.

The reference electrode 6 is configured to provide a reference potential so that potential changes caused by an equilibrium reaction or a chemical reaction, which occurs on a surface of the working electrode in a liquid for measurement, are stably measured.

Generally, although a silver or silver/chloride electrode having a saturated potassium chloride solution contained therein is used or a calomel electrode is used as the reference electrode 6, it is allowable to use only the silver/silver chloride electrode as a pseudo electrode when composition of a sample fluid to be measured is stable.

Figure 4:
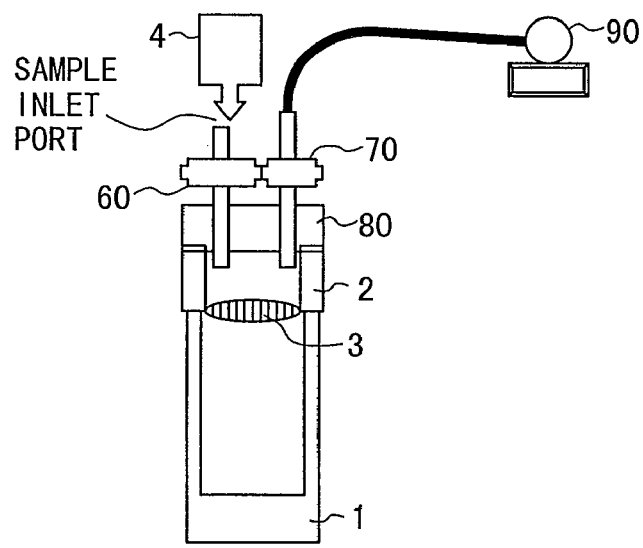
FIG. 4 is a view illustrating a separation unit such as a filter and a sample vessel with a pressure pump in Embodiment 3 of the present invention.

FIG. 4 is a view illustrating a pressure type fractionating device. The supporting body 2 is detachably placed on the sample vessel 1 having a cylindrical form with a bottom. The supporting body 2 has a cylindrical form, and has the filter 3 for fractionation provided inside but at a lower portion thereof. A sample injection valve 60 and a pressure pump connection valve 70 are incorporated in a valve supporting body 80 above the sample vessel 1. The sample injection valve 60 and a pressure pump connection valve 70 are connected to sample vessel 1 with the filter fixed on the supporting body 2 held therebetween. A micro pump 90 is connected to the pressure pump connection valve 70.

The filter 3 for fractionation is mainly made of a mixture of nitrocellulose and cellulose acetate, and the materials used have fine pores each having a diameter of 0.8 μm or below.

A precipitant for lipoproteins other than HDL is infiltrated in this filter 3 for fractionation to form a carrier. The filter 3 for fractionation is used as a base material for a carrier. The carrier serves as a separation unit.

A sample for measurement is in the sample injection vessel 4. The sample is injected from the sample injection vessel 4 into the sample injecting section. When the micro pump is actuated for pressurizing, the sample, which is a biological fluid, circulates through the filter 3 for fractionation with lipoproteins other than HDL separated, and high density lipoproteins flows through the filter 3 for fractionation into the sample vessel 1.

As described above, when a carrier thus-prepared by infiltrating the filter 3 for fractionation with a precipitant for lipoproteins is used, lipoproteins other than HDL can quickly be separated from a biological fluid.

Figure 5:
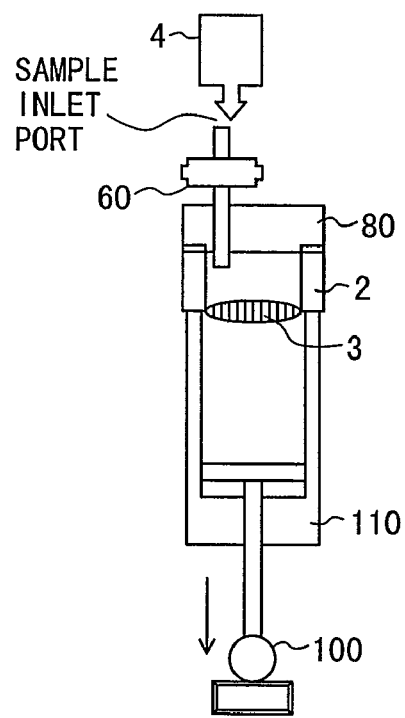
FIG. 5 is a view also illustrating a separation unit such as a filter and a sample vessel with a syringe pump in Embodiment 3 of the present invention.

FIG. 5 is a view illustrating a negative pressure type fractionating device. This embodiment employs a syringe type sample vessel. The supporting body 2 is detachably placed on the syringe type sample vessel 110. The supporting body 2 has a cylindrical form, and has the filter 3 for fractionation provided inside but at a lower portion thereof. The sample injection valve 60 is incorporated in the valve supporting body 80 above the sample vessel 110. The sample injection valve 60 is connected to the sample vessel 110 with the filter fixed on the supporting body 2 held therebetween. A syringe pump 100 is connected below the sample vessel 110.

The filter 3 for fractionation is mainly made of a mixture of nitrocellulose and cellulose acetate, and the materials used have fine pores each having a diameter of 0.8 μm or below.

A precipitant for lipoproteins other than HDL is infiltrated in this filter 3 for fractionation to form a carrier. The filter 3 for fractionation is used as a base material for a carrier. The carrier serves as a separation unit.

A sample for measurement is in the sample injection vessel 4. The sample is injected from the sample injection vessel 4 into the sample injecting section. When the syringe pump 100 is actuated to generate a negative pressure, the sample, which is a biological fluid, circulates through the filter 3 for fractionation with lipoproteins other than HDL separated, and high density lipoproteins flows through the filter 3 for fractionation into the sample vessel 110.

As described above, when a carrier thus-prepared by infiltrating the filter 3 for fractionation with a precipitant for lipoproteins is used, lipoproteins other than HDL can quickly be separated from a biological fluid.

Figure 6:
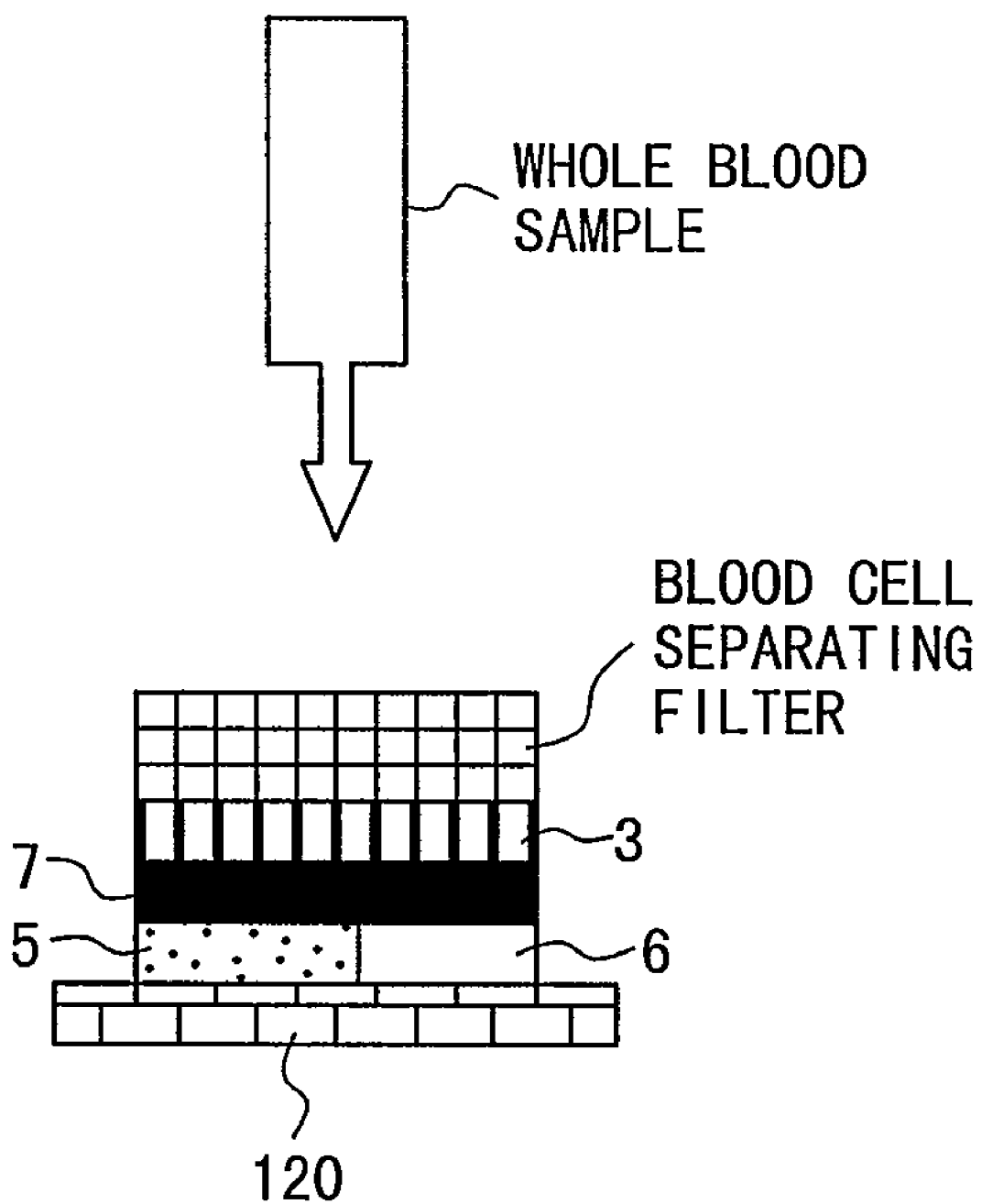
FIG. 6 is a view illustrating a sample vessel including a working electrode and a reference electrode which are used for a whole blood sample in Embodiment 3 of the present invention.

FIG. 6 is a view illustrating an integrated type analysis device for a whole blood sample. The filter 3 fractionating and the working electrode 5 and reference electrode 6 in contact with this filter 3 are provided above an electrode supporting body 120. The reagent layer 7 is provided on the working electrode 5. A blood cell separating filter is provided in contact with the filterer 3 for fractionating so that a whole blood sample may be used. The reagent layer 7 reacts with the sample for measurement and contributes to the measurement.

The filter 3 for fractionation is mainly made of a mixture of nitrocellulose and cellulose acetate, and the materials used have fine pores each having a diameter of 0.8 μm or below.

A commercially available filter products can be used as the blood cell separating filter. Any of cellulose, nylon, polysulfone, or the like can be used as a material for the filter 3.

A precipitant for lipoproteins other than HDL is infiltrated in this filter 3 for fractionation to form a carrier. The filter 3 for fractionation is used as a base material for a carrier. The carrier serves as a separation unit.

When the whole blood sample, which is a biological fluid, is dripped onto the blood cell separating filter, the blood cells are separated, and the plasma flows through the filter 3 for fractionation with the lipoproteins other than HDL separated, while the high density lipoproteins pass through the filter 3 for fractionation. The material as an object for measurement precipitated and separated in the sample fluid reacts with a reagent for reaction with the materials to be measured, with the result that an electric charge is generated on a surface of the working electrode 5. As a result, an interface potential on the working electrode 5 changes.

As described above, when a carrier thus-prepared by infiltrating the filter 3 for fractionation with a precipitant for lipoproteins is used, lipoproteins other than HDL can quickly be separated from a biological fluid.

Figure 7:
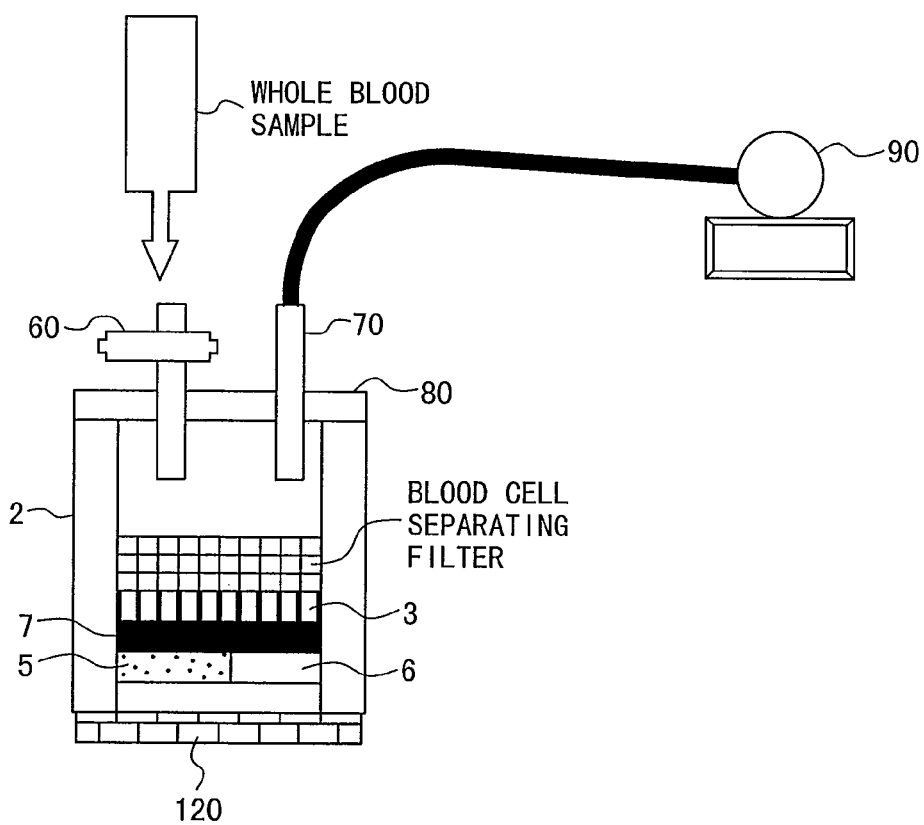
FIG. 7 is a view illustrating a separation unit such as a filter and a sample vessel with a pressure pump, and the like which are used for a whole blood sample in Embodiment 3 of the present invention.

FIG. 7 is a view illustrating a pressure type integrated measuring device for a whole blood sample. The filter 3 fractionating and the working electrode 5 and reference electrode 6 in contact with this filter 3 are provided above an electrode supporting body 120. The reagent layer 7 is provided on the working electrode 5. The blood cell separating filter is provided in contact with the filterer 3 for fractionating so that a whole blood sample may be used. The sample injection valve 60 and the pressure pump connection valve 70 are incorporated in the valve supporting body 80 above the sample vessel. The sample injection valve 60 and the pressure pump connection valve 70 are connected to the sample vessel with the filter fixed on the supporting body 2 held therebetween. The micro pump 90 is connected to the pressure pump connection valve 70. The reagent layer 7 reacts with the sample for measurement and contributes to the measurement.

A sample for measurement is in the sample injection vessel 4. The sample is injected from the sample injection vessel 4 into the sample injecting section. When the micro pump is actuated for pressurizing, the sample, which is a biological fluid, circulates through the filter 3 for fractionation with lipoproteins other than HDL separated, and high density lipoproteins flows through the filter 3 for fractionation. The material as an object for measurement precipitated and separated in the sample fluid reacts with a reagent for reaction with the materials to be measured, with the result that an electric charge is generated on a surface of the working electrode 5. As a result, an interface potential on the working electrode 5 changes.

The filter 3 for fractionation is mainly made of a mixture of nitrocellulose and cellulose acetate, and the materials used have fine pores each having a diameter of 0.8 μm or below.

A commercially available filter products can be used as the blood cell separating filter. Any of cellulose, nylon, polysulfone, or the like can be used as a material for the filter 3.

A precipitant for lipoproteins other than HDL is infiltrated in this filter 3 for fractionation to form a carrier. The filter 3 for fractionation is used as a base material for a carrier. The carrier serves as a separation unit.

As described above, when a carrier thus-prepared by infiltrating the filter 3 for fractionation with a precipitant for lipoproteins is used, lipoproteins other than HDL can quickly be separated from a biological fluid.

Figure 8:
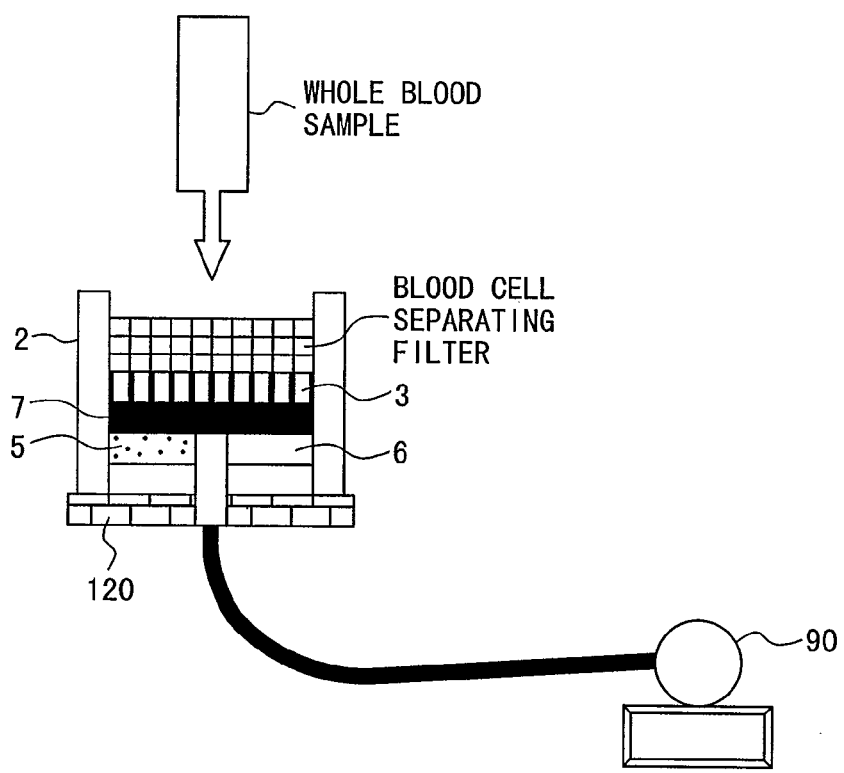
FIG. 8 is a view illustrating a separation unit having a sample vessel with a syringe pump, a filter, and the like which are used for a whole blood sample in Embodiment 3 of the present invention.

FIG. 8 is a view illustrating a negative type integrated analysis device for a whole blood sample. The filter 3 for fractionation, the working electrode 5 contacting the filter 3, and the reference electrode 6 are provided above the electrode supporting body 120. A enzymatic reagent layer 7 is provided on the working electrode 5. The blood cell separating filter is provided in contact with the filterer 3 for fractionating so that a whole blood sample may be used. The micro pump 90 is connected to a lower portion of the enzymatic reagent layer 7.

The filter 3 for fractionation is mainly made of a mixture of nitrocellulose and cellulose acetate, and the materials used have fine pores each having a diameter of 0.8 µm or below.

A sample for measurement is in the sample injection vessel 4. The sample is injected from the sample injection vessel 4 into the filter. When the micro pump is actuated to generate a negative pressure, the sample, which is a biological fluid, circulates through the filter 3 for fractionation with lipoproteins other than HDL separated, and high density lipoproteins flows through the filter 3 for fractionation. The material as an object for measurement precipitated and separated in the sample fluid reacts with a reagent for reaction with the materials to be measured, with the result that an electric charge is generated on a surface of the working electrode 5. As a result, an interface potential on the working electrode 5 changes.

A commercially available filter products can be used as the blood cell separating filter. Any of cellulose, nylon, polysulfone, or the like can be used as a material for the filter 3.

A precipitant for lipoproteins other than HDL is infiltrated in this filter 3 for fractionation to form a carrier. The filter 3 for fractionation is used as a base material for a carrier. The carrier serves as a separation unit.

As described above, when a carrier thus-prepared by infiltrating the filter 3 for fractionation with a precipitant for lipoproteins is used, lipoproteins other than HDL can quickly be separated from a biological fluid.

What is claimed is:

1. A method of separating lipoproteins other than high density lipoprotein (HDL) from a biological fluid, the method comprising the steps of:
    mixing a biological fluid containing the lipoproteins other than HDL with a precipitant for the lipoproteins other than HDL to precipitate the lipoproteins other than HDL; and
    circulating a precipitation liquid precipitated in the precipitating step through a carrier made of a mixture of nitrocellulose and cellulose acetate and having a pore diameter of 0.8 µm or below, wherein the precipitant is a polyanion in combination with a bivalent metal ion.

2. The method of separating lipoproteins other than HDL from a biological fluid according to claim 1, wherein the step of mixing a biological fluid containing the lipoproteins other than HDL with a precipitant includes mixing the biological fluid with one of heparin-Ca precipitant, phosphotungustic acid-Mg precipitant, and dextran sulfate Mg-phosphotungustic acid-Mg precipitant to precipitate the lipoproteins other than HDL.

* * * * *